(12) United States Patent
Guenter et al.

(10) Patent No.: US 9,770,312 B2
(45) Date of Patent: Sep. 26, 2017

(54) DENTAL IMPLANT SOCKET ARRANGEMENT

(71) Applicant: STRAUMANN HOLDING AG, Basel (CH)

(72) Inventors: Daniel Guenter, Basel (CH); Stephane Courvoisier, Basel (CH); Miodrag Lazic, Basel (CH); Florian Dalla Torre, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 0 days.

(21) Appl. No.: 14/897,386

(22) PCT Filed: Jun. 9, 2014

(86) PCT No.: PCT/EP2014/061939
§ 371 (c)(1),
(2) Date: Dec. 10, 2015

(87) PCT Pub. No.: WO2014/198681
PCT Pub. Date: Dec. 18, 2014

(65) Prior Publication Data
US 2016/0143708 A1  May 26, 2016

(30) Foreign Application Priority Data
Jun. 10, 2013 (EP) .................................... 13171311

(51) Int. Cl.
*A61C 8/00* (2006.01)
(52) U.S. Cl.
CPC ............ *A61C 8/006* (2013.01); *A61C 8/0018* (2013.01); *A61C 8/0022* (2013.01); *A61C 8/0089* (2013.01)

(58) Field of Classification Search
CPC ..... A61C 8/006; A61C 8/0018; A61C 8/0089; A61C 8/0022; A61C 8/0066; A61C 8/0068; A61C 8/0069
(Continued)

(56) References Cited

U.S. PATENT DOCUMENTS 5,076,788 A    12/1991  Niznick
6,733,291 B1 *  5/2004  Hurson ................ A61C 8/0054
                                                                    433/173
(Continued)

FOREIGN PATENT DOCUMENTS

EP    1128778 B1    5/2005
EP    1 419 746 B1  6/2011
EP    1427348 B1    6/2012

OTHER PUBLICATIONS

Sep. 10, 2014 Search Report issued in International Patent Application No. PCT/EP2014/061939.

*Primary Examiner* — Pedro Philogene
*Assistant Examiner* — David C Comstock
(74) *Attorney, Agent, or Firm* — Oliff PLC (57) ABSTRACT

Dental implant having a socket arrangement having the shape of a regular octagon which is partly interrupted by outwardly extending notches being parallel or parallel and partly inclined with respect to the longitudinal center axis of the implant, the inclination being such as to taper inwardly from their coronal end, wherein interrupting and outwardly extending ridges extending from the notches in an apical direction of the dental implant, first contact surfaces being adapted to engage and rotationally secure an abutment, and wherein second contact surfaces extend from the notches within the ridges in the direction of the longitudinal center axis, the second contact surfaces being adapted to engage (Continued)

with an insertion tool; and wherein the notches are positioned at sides or at corners of the regular octagon.

15 Claims, 10 Drawing Sheets

(58) Field of Classification Search
USPC .......................................................... 433/174
See application file for complete search history.

(56) References Cited

U.S. PATENT DOCUMENTS

| | | | |
|---|---|---|---|
| 2002/0177105 A1* | 11/2002 | Engman | A61C 8/005 433/173 |
| 2010/0248181 A1 | 9/2010 | Kremer et al. | |
| 2010/0304329 A1* | 12/2010 | Heo | A61C 8/0089 433/146 |
| 2011/0143316 A1 | 6/2011 | Olson et al. | |
| 2012/0196247 A1 | 8/2012 | Bugnard et al. | |

* cited by examiner

DENTAL IMPLANT SOCKET ARRANGEMENT

FIELD OF THE INVENTION

The present invention relates in general to a dental implant intended to be screwed into the jawbone for supporting at least one abutment. The present invention furthermore relates in particular to an improved socket arrangement of the dental implant cooperating on the one hand with an insertion tool and on the other hand with the abutment. Furthermore, the present invention relates to the insertion tool adapted to engage with the socket arrangement of the dental implant.

PRIOR ART

As known in the art, a threaded dental implant intended to be screwed into the jawbone for supporting at least one abutment must have a certain socket arrangement with lateral contact surfaces and an upper contact surface whereon the abutment can be fixed for a long time in a determined stable position. Furthermore, as known in the art, the threaded dental implant needs to be screwed into the jawbone with certain torque forces of up to approximately 150 Ncm. During this screwing operation the problem has to be faced that the insertion tool, which is for instance an Allen wrench engaging with an Allen socket as part of the socket arrangement, could cause a material welding or shifting within respective lateral contact surfaces of the Allen socket. Thus, if the same lateral contact surfaces would be used for the positioning of the abutment and the engagement with the insertion tool, or in other words if the first contact surfaces would be the second contact surfaces, there exists the risk that the abutment would not fit anymore in the implant in the determined position due to changes in the socket.

EP 1 427 348 B1 discloses a threaded dental implant with a socket arrangement with the first contact surfaces engaging with the abutment and with the same first contact surfaces engaging with the insertion tool.

EP 1 128 778 B1 discloses a threaded dental implant with a socket arrangement with the first contact surfaces engaging with the abutment and with the second contact surfaces engaging with the insertion tool, wherein the first contact surfaces are devised, preferably, on an outside part of a coronal end of the implant and the second contact surfaces are devised inside the coronal end of the implant. Thus the first and the second contact surfaces are completely geometrically separated. However, the production of the above known implant is more difficult and expensive, inasmuch one has to mill two totally separate parts of the socket arrangement, once outside and once inside the coronal end of the implant. By geometrically separating the first and the second contact surfaces one to outside and the other to the inside of the coronal end of the implant, the inner second contact surfaces get necessarily closer to a longitudinal center axis of the implant with the consequence that higher contact forces occur to produce the torque necessary for screwing the implant into the jawbone, as compared with a situation in which the second contact surfaces have a longer lever arm. The presence of higher contact forces increases the welding risk of the material of the socket and can even influence and cause a deformation of the outer first contact surfaces. The welding of the socket material or the deformation thereof could lead to a more difficult disengagement between the insertion tool and the implant, as a jamming or gripping may occur, or to a worse or even an impossible engagement between the implant and the abutment.

EP 1 419 746 B1 discloses a threaded dental implant with a socket arrangement where the first anti-rotational means, e.g. a polygonal contact surface is separate from the second anti-rotational means, inasmuch as the second anti-rotational polygonal contact surface lies longitudinally separate from the first anti-rotational means. However, having two longitudinally separate anti-rotational means results in an unfavorable deep socket of the implant, which limits the total possible length of the implant substantially.

In the context of the present invention the wording "implant" stands herein for dental implant or, preferably, threaded dental implant. Further, in the context of the present invention the wording "abutment" stands herein also for a superstructure being connected directly to at least one implant and carrying or adapted to carry one or more artificial teeth or crowns.

SUMMARY OF THE INVENTION

The objective of the invention is to overcome the shortcomings explained above and to provide a, preferably threaded, dental implant with a socket arrangement cooperating with an insertion tool for screwing the implant into the jawbone and acting to keep an abutment in a defined position for a long time, such that a first part of the socket arrangement for positioning the abutment on the implant does not get affected by a second part of the socket arrangement for engaging with the insertion tool forces.

The above objectives as well as further objectives which will also become apparent from the following description are achieved by the features of a, preferably threaded, dental implant and by an insertion tool mentioned in the independent claims 1 and 14, respectively. Additional features and characteristics of the invention are mentioned in the dependent claims.

Advantageously the present invention allows for the engagement between the insertion tool for screwing the dental implant into the jawbone and the dental implant with much longer arm levers in respect to a longitudinal center axis of the implant as compared to a situation in which the outer and coronal surface of the implant had to be milled or lathed for providing another outer socket for an abutment, inasmuch as the outer diameter of the coronal end of the implant is not reduced. The longer arm levers for transmitting necessary forces via second contact surfaces, in order to achieve a certain torque for the screwing in the implant into the jawbone, result in smaller forces at the second contact surfaces. Smaller forces, again, cause less material strain at the second contact surfaces, in particular if the second contact surfaces have an angle perpendicular to the respective resulting force thereat. Alternatively, the second contact surfaces can be devised smaller, for instance, such that resulting notches as cross-sectional shape of the second contact surfaces have a lesser extension in radial direction. Thus both, the second contact surfaces for transmitting the insertion torque from the insertion tool, and first contact surfaces for longtime engaging with the abutment, have a longer arm lever resulting in better force transmission, bigger respective contact surfaces and less welding or deformation of the respective contact surfaces, as compared with smaller arm levers. Longer arm levers can be attained if the implant is not reduced in its outer diameter as is it would be the case if an outer coronal socket is provided.

Also a coronal upper contact surface between the implant neck and the abutment devised according to the present invention, which defines the height of the abutment on the implant, is much larger than a prior art coronal upper contact surface wherein the coronal lateral surface would be milled or lashed or otherwise removed.

Also, by avoiding a lathing or milling of both the coronal lateral surface and a coronal inside of the implant, as required by the prior art, and instead lathing, milling or machining only inside the coronal end of the implant machine, time and cost can be saved.

Advantageously, according to the invention, the first and the second contact surfaces are arranged at a same height along the longitudinal axis of the implant and close to the coronal end thereof, such as to achieve longer arm levers between the implant and the insertion tool or abutment, respectively. This allows a close and good force and torque transmission between the implant and the insertion tool as well as between the implant and the abutment. Furthermore and in contrast to the prior art, the present invention allows for a minimal ingression into the socket, inasmuch as lateral wall thickness perpendicular to the longitudinal axis of the dental implant is maintained while at the same time a minimal total implant length parallel to the longitudinal axis is offered.

An octagonal cross-sectional arrangement of the first contact surfaces provides for a particularly advantageous aspect of the invention, as the outer surface of an octagon is larger as compared with a surface of a hexagon with the same height and circumference. Thus, an octagonal cross-sectional socket with the respective eight first contact surfaces has a larger contact area engaging with the abutment than a hexagonal cross-sectional socket and still good enough anti-rotational resistance for the abutment on the implant. By the larger first contact surfaces higher lateral forces between the abutment and the implant can be applied without deforming the implant. In respect to the first contact surfaces a torque force around the longitudinal center axis of the implant is much lower than for the second contact surfaces, as the abutment does not apply a torque as high as the insertion tool does. The torque transmitting surface for the insertion tool increases with the number of notches and respective ridges extending in the longitudinal direction from the respective coronal cross-sectional notches and having the respective second contact surfaces. Thus also a number of up to eight notches can be devised according to the torque for screwing in the implant, and/or according to the material strength and thickness of the remaining coronal lateral sidewall of the implant at the height of the first and second contact surfaces.

The invention is set forth and characterized in the main claims, while dependent claims describe other advantageous characteristics of the invention.

Preferred embodiments according to the present invention are disclosed in the following drawings and in the detailed description but it shall not be interpreted as limiting the invention.

BRIEF DESCRIPTION OF THE DRAWINGS

FIG. 2d is a variation of FIG. 2a with second contact surfaces having a cross-section which differs from that of FIG. 2a.

FIG. 3d is a variation of FIG. 3a with second contact surfaces having a cross-section which differs from that of FIG. 3a.

DETAILED DESCRIPTION OF A PREFERENTIAL EMBODIMENTS OF THE INVENTION

Figure 1:
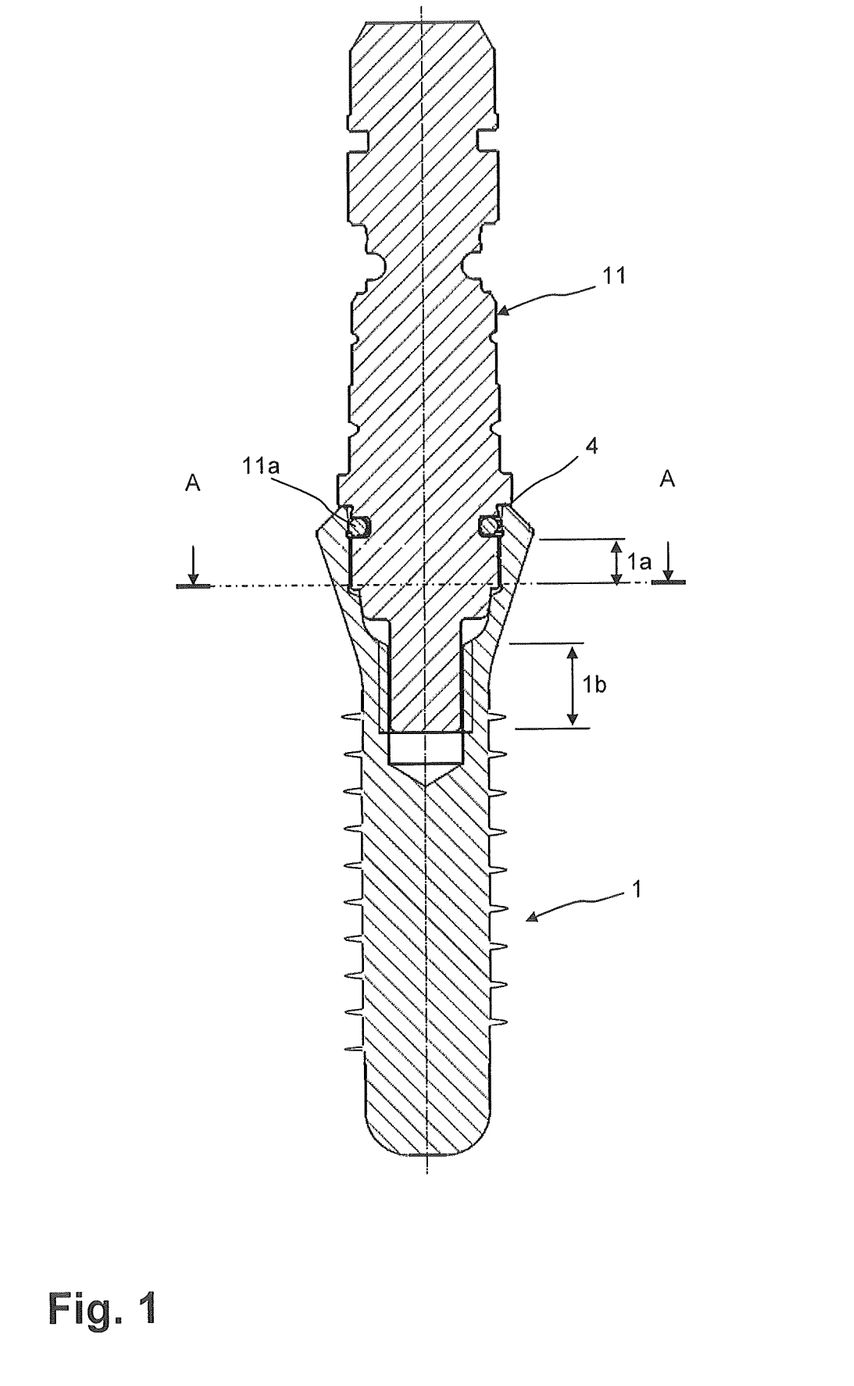
FIG. 1 is a cross-sectional side view drawing of a threaded dental implant.

FIG. 1 shows a cross-sectional side view of a threaded dental 1 implant with an insertion tool or a transfer piece 11 (hereinafter for the sake of simplicity only designated as insertion tool) engaged with a coronal portion thereof. Although in the following only threaded dental implants are shown or mentioned as preferred embodiments, it should be born in mind that the present invention is equally applicable to non-threaded dental implants. The outer part of an apical portion of the implant 1 carries an external thread. The external thread comprises preferably self-cutting means as for instance sharp recesses or grooves, not shown, such that the implant 1 can cut its thread in a jawbone. For an insertion of the implant 1 in the jawbone the insertion tool 11 is temporarily connected with the implant 1 for the insertion. Preferably the jawbone comprises an appropriate hole for the implant 1. During the insertion of the implant in the jawbone there occur torques of up to approximately 150 Ncm which have to be transmitted from the insertion tool 11 to the implant. After the implant 1 has been inserted in the jawbone and after engraftment, an abutment, which is not shown, is placed and fixed onto the coronal end of the implant 1, wherein the positioning of the abutment must be possible precisely and in a determined height as well as in a defined rotational position or angle. As shown in FIG. 1 the insertion tool 11 has a resilient O-Ring or a split C-Ring 11a mounted thereon and engaged in a coronal end part thereof.

The implant 1 comprises a socket arrangement with a first and a second section with respective geometrical profiles within at least a height 1a of the socket arrangement, wherein the socket arrangement is devised to cooperate by means of its second section with the insertion tool 11 and by means of its first section with the abutment for rotationally securing the respective insertion tool 11 or the abutment. The first and second sections are arranged at the coronal portion of the implant in an internal open ended axial bore thereof. For fixing the abutment on the implant 1 by a screw, the implant 1 comprises preferably an internal thread within a threaded section 1b below the height 1a of the socket in apical direction. As shown, the threaded section 1b is preferably also used as a guiding and axial stabilizing means for the insertion tool 11. A preferred insertion tool 11 comprises, as mentioned, the resilient O-ring or a split C-Ring 11a for engaging with the implant with little force, such little that the insertion tool 11 can be disengaged from the implant 1 easily after insertion into the bone, and on the other hand so strong that the implant 1 is held in the insertion tool 11 and doesn't fall off during transport to the patients mouth.

For securing the abutment in a determined position against the implant 1, the implant 1 comprises at its upper end or close thereof a coronal upper contact surface 4 against which the abutment is pressed in order to define the height of the abutment in direction of the a longitudinal center axis of the implant 1.

FIGS. 2a to 2d show variations of a first embodiment of the invention along a cross-sectional top view of dental implants taken along line A-A of FIG. 1, which are reduced to the representation of a cross-section of the socket arrangement at the bottom of the first and the second section. For the sake of clarity it should be noted that FIGS. 2a to 5b show cross-sectional discs cut out from the implant 1 perpendicular to its longitudinal axis.

The first section of the socket arrangement defines first contact surfaces 3 having partly a cross-sectional shape of a polygon and preferably a regular polygon. The first contact surfaces 3 are extending from the coronal end downwardly in apical direction of the longitudinal center axis of the implant 1 along the height 1a of the socket, and are parallel to the longitudinal axis of the implant. Nevertheless, the first contact surfaces 3 may be partly cut out by inclined parts or truncated conical sections 3b, the truncated conical sections (3b) forming partly a truncated cone within the height 1a of the socket. However, the contact with the abutment occurs at the sections of the first contact surface 3 which are parallel to the longitudinal axis of the dental implant but not at the inclined parts or truncated conical sections 3b. The first contact surfaces 3 are devised as sides of the polygon. The polygonal shaped first contact surfaces 3 are partly interrupted by outwardly extending notches 2 at which longitudinally extending ridges are defined, the ridges comprising second contact surfaces 2a and 2b. In the variations of the first embodiment of FIGS. 2a through 2d the interruptions of the first contact surfaces 3 are within the corners of the polygon. In the context of the present invention the notches 2 are defined as cross-sections in the ridges, the ridges extending as explained in the longitudinal direction of the dental implant 1. The ridges include a lateral surface 2c extending between the second contact surfaces 2a and 2b. The first contact surfaces 3 are adapted to engage with the corresponding contact surfaces of the abutment (not shown). The ridges are preferably truncating into a tapered section. The machining or production of the first contact surfaces can be done by a CNC milling machine, but the machining or production of the first contact surfaces by a cold forming operation like chipping or eroding, which for shapes as herein described is faster than milling operations, is preferred.

The first contact surfaces 3 partly merge to the second contact surfaces 2a, 2b, preferably with a respective transition surface. The first contact surfaces 3 are the surfaces of the socket arrangement which correspond to the respective contact surfaces of the abutment, and the second contact surfaces 2a, 2b are the surfaces of the socket arrangement which correspond to the respective contact surfaces of the insertion tool 11.

Figure 2A:
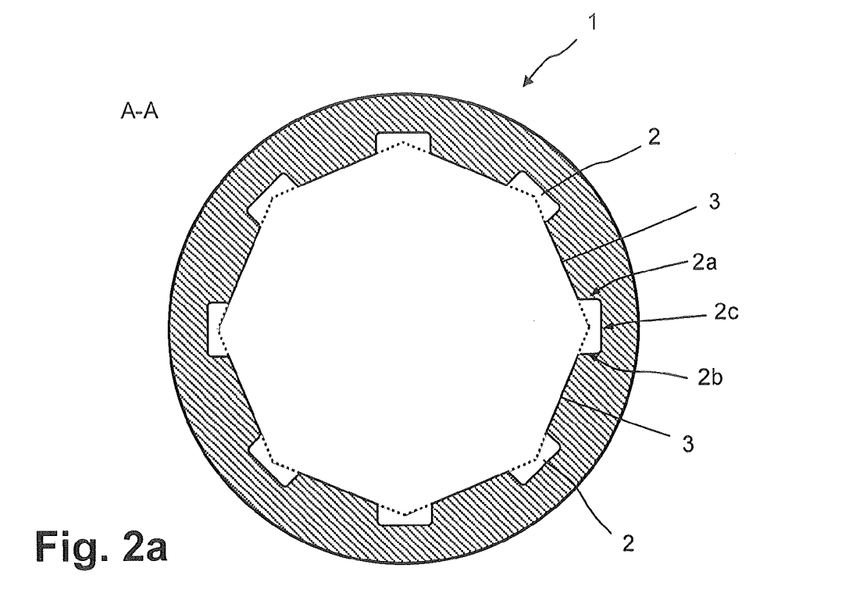
FIG. 2a is a cross-sectional top view drawing of a first embodiment of the threaded dental implant reduced to a socket arrangement with first contact surfaces for engaging with an abutment and with second contact surfaces for engaging with the insertion tool, wherein the second contact surfaces have a rectangular cross-sectional shape.
Figure 2B:
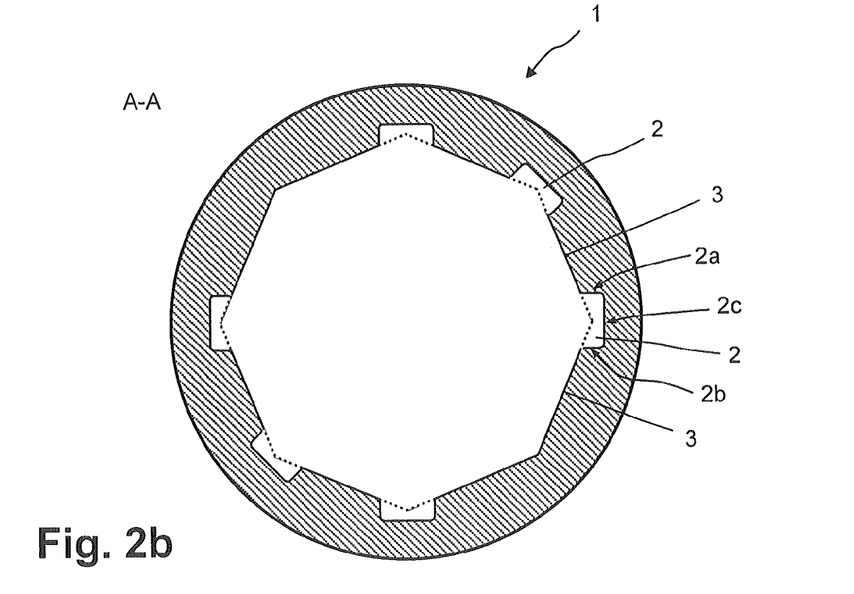
FIG. 2b is a variation of FIG. 2a with a lesser number of second contact surfaces.
Figure 2C:
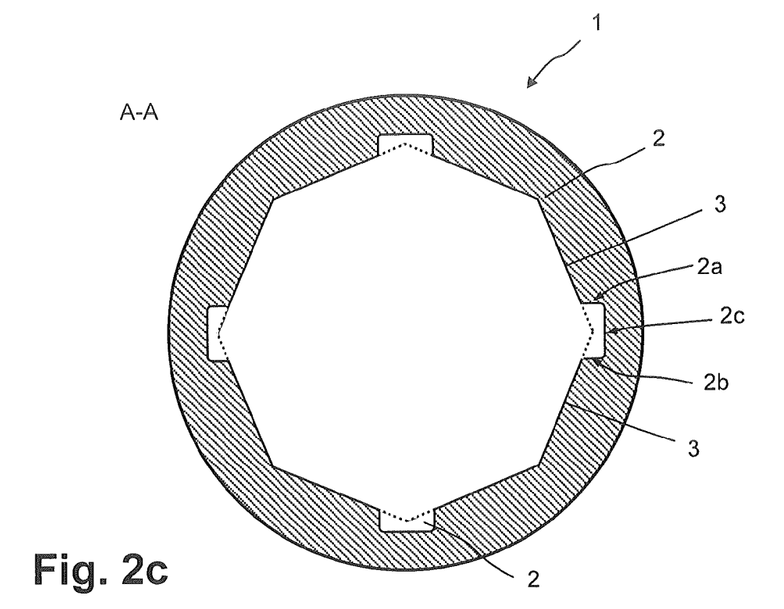
FIG. 2c is a variation of FIG. 2a with a lesser number of second contact surfaces.

The notches 2 extending outwardly in radial direction of the polygonal shape of the first contact surfaces 3 are in the variations of the first embodiment according to FIGS. 2a through 2c shaped preferably rectangular or substantially rectangular. Thus, the respective ridges are shaped in the same manner. As a matter of fact, whenever in the context of the present invention a certain shape of the notch 2 is described, the corresponding ridge is understood to have consistently the same shape in its cross-section. Preferably the second contact surfaces 2a and 2b are positioned at sides of the respective notch 2 at an area engaging with the insertion tool 11. Preferably said second contact surfaces 2a and 2b are positioned and arranged, such that they are angled perpendicularly to torque forces applied by respective contact surfaces of the insertion tool 11. Alternatively said second contact surfaces 2a and 2b are positioned and arranged, such that they are angled to the torque forces applied by the respective contact surfaces of the insertion tool 11 substantially perpendicular with a tolerance of equal or less than 10 degrees. Preferably the second contact surfaces 2a and 2b are adapted to be parallel to the contact surfaces of the ribs of the insertion tool 11 applying said torque forces.

The notches 2 and ridges, respectively, devised at the corners of the polygonal shape of the first contact surfaces 3 allow having a sufficient large area of the first contact surfaces 3, and further having contact surfaces 2a, 2b with a large diagonal distance between one notch 2 and an opposite notch 2.

Preferably said second contact surfaces 2a face with its respective orthogonal vector substantially into a respective first tangential direction with respect to the longitudinal center axis of the implant 1, and said second contact surfaces 2b face with its respective orthogonal vector substantially into a respective second tangential direction with respect to the longitudinal center axis of the implant 1.

Figure 2D:
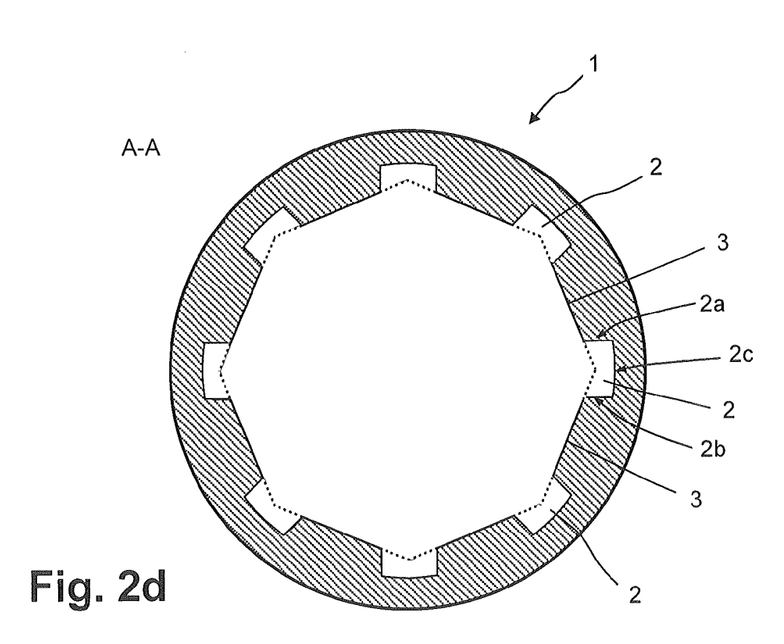

Alternatively the notches 2 are shaped as laterally slightly curved notches 2, as shown in FIG. 2d, wherein the lateral surface 2c is devised as a laterally curved surface being comprised between said second contact surfaces 2a and 2b.

Preferably the laterally curved surface is a segment of a cylindrical or truncated conical surface, such that no torque is transmitted via said laterally curved surface with respect to a rotation around the longitudinal center axis of the implant 1, and the torque is transmitted substantially only by the second contact surfaces 2a, 2b.

Preferably the polygon is an octagon, which has advantageously longer side walls or first contact surfaces 3 with a same diagonal as for instance a polygon with less corners such as a hexagon.

With an increasing number of notches 2 or ridges the possible transmittable torque increases as well. Thus, a preferred embodiment with an octagonal cross-sectional shape of the first contact surfaces 3 is advantageously featuring respective large contact areas of the first 3, while the second contact surfaces 2a, 2b allow higher transmittable lateral forces and torque forces between the implant 1 and the abutment or the insertion tool 11. Thus, a maximum number of eight notches 2 or ridges, is providing a lower stress concentration on a single notch or ridge during torque transmission than a number of six or four notches, and accordingly for a better torque function.

As shown in FIGS. 2a to 2c, the number of the notches or ridges can vary. Same applies for the position of the notches or ridges at the corners of the polygon which many be adjacent or spaced by one or more corners of the polygon. At any rate, the choice of the number and positions of the notches or ridges is made by the person skilled in the art in order to optimize the torque transmission while allowing for sufficient area to subsequently position the abutment in a stable angular position. In addition, if the notches or ridges are placed adjacent to another, like for instance having the lateral notches or ridges of FIG. 2c placed adjacent to the upper and lower notches/ridges respectively, manufacturing advantages are attained, in particular if the notches or ridges are obtained by cold forming. The same variations and considerations apply to the notches or ridges shown in FIG. 2d.

Figure 3A:
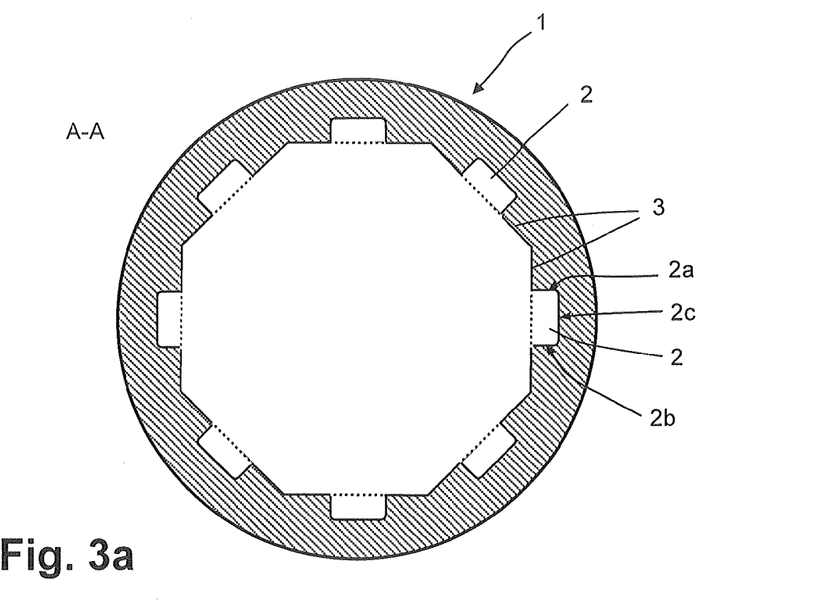
FIG. 3a is a cross-sectional top view drawing of a second embodiment of the threaded dental implant reduced to another socket arrangement with the first contact surfaces and with the second contact surfaces, wherein the second contact surfaces have a rectangular cross-sectional shape.
Figure 3B:
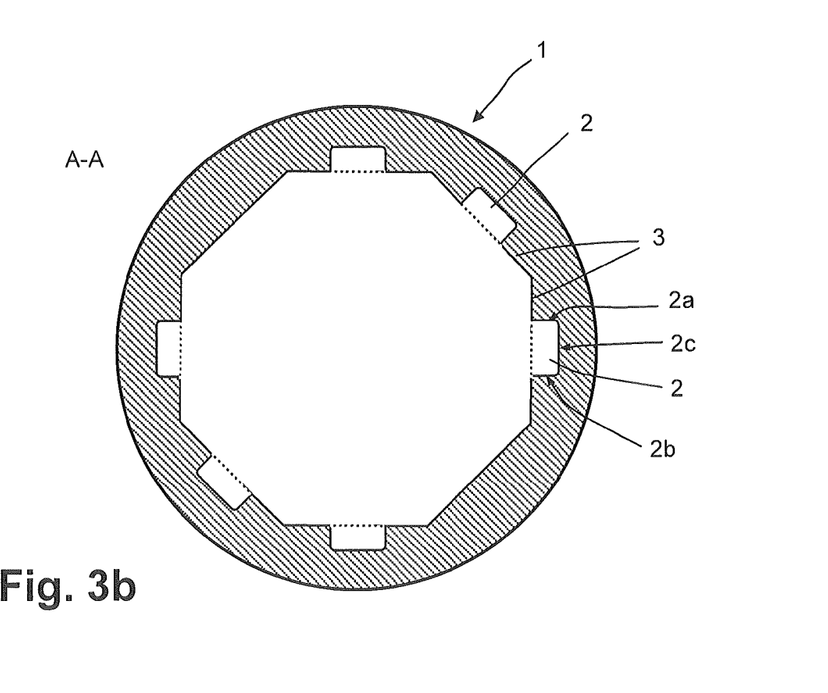
FIG. 3b is a variation of FIG. 3a with a lesser number of second contact surfaces.
Figure 3C:
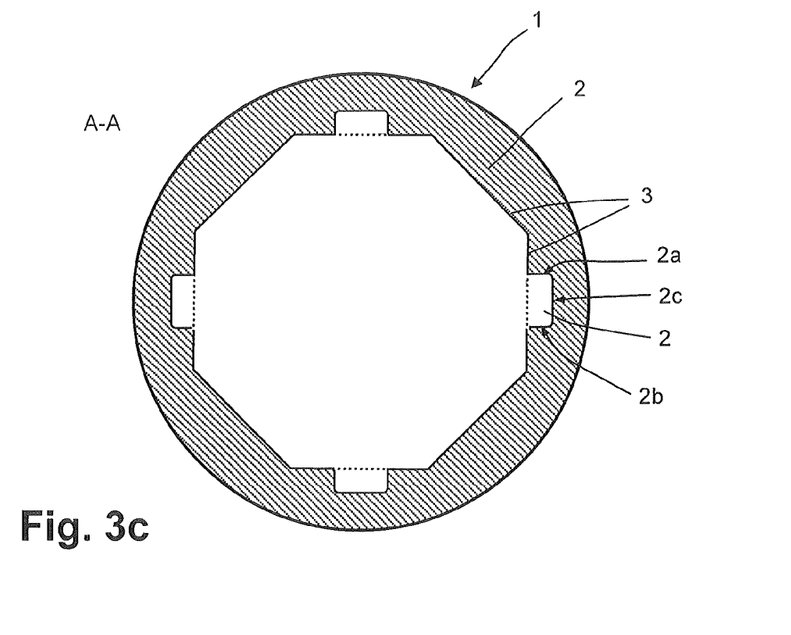
FIG. 3c is a variation of FIG. 3a with a lesser number of second contact surfaces.
Figure 3D:
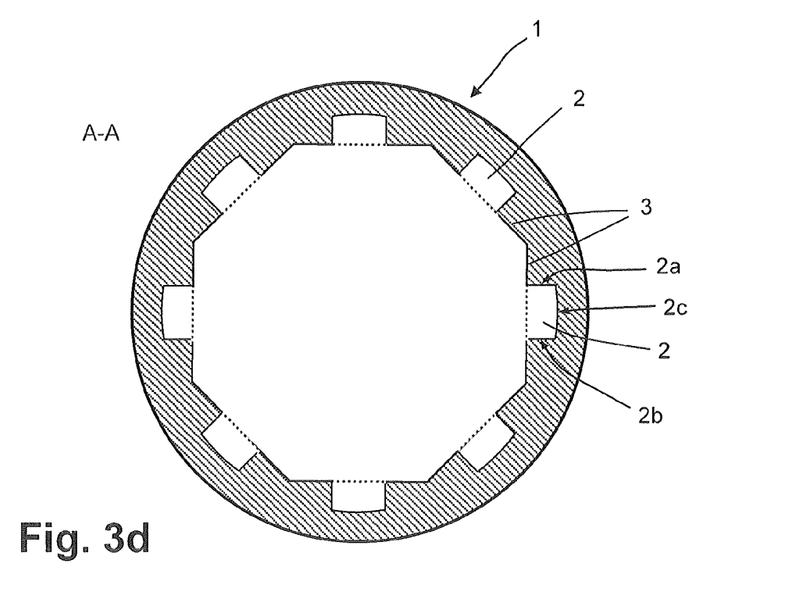

FIGS. 3a to 3d are representations of a cross-sectional top view of variations of a second preferred embodiment of the threaded dental implant, which is simplified in the drawing to a disk like cross-section of the socket arrangement, similar to that of FIGS. 2a to 2d. The only difference between the first embodiment of FIGS. 2a to 2d and the second embodiment of FIGS. 3a to 3b is that in the latter embodiment the notches 2 or ridges are devised within the middle of the respective sides of the polygonal shape of the first contact surfaces 3. Otherwise, all considerations set out in conjunctions with the first embodiment (namely the variations of the first embodiments of FIGS. 2a to 2b) are fully applicable. In addition, in the variations of the second embodiment, as the contact surfaces 2a, 2b are devised in the middle of the first contact surfaces 3, the notches 2 may feature a larger radial depth and thus a larger contact area as compared with the notches 2 that are positioned at the corners of the polygon in accordance with the variations of the first embodiment. Thus, a larger surface area is available for distributing the torque.

Figure 4A:
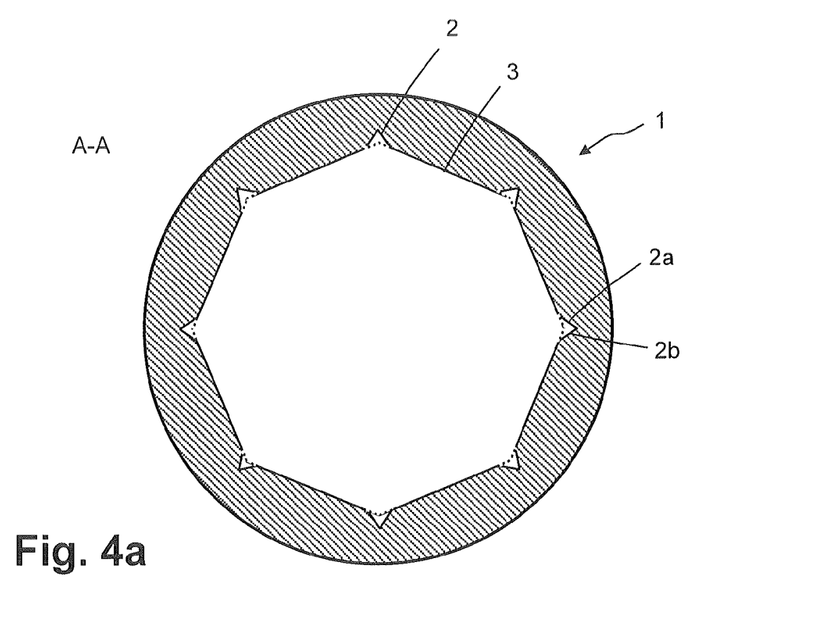
FIG. 4a is a cross-sectional top view drawing of a third embodiment of the threaded dental implant reduced to another socket arrangement with the first contact surfaces and with the second contact surfaces, wherein the second contact surfaces are in the form of eight notches having a triangular cross-sectional shape.
Figure 4B:
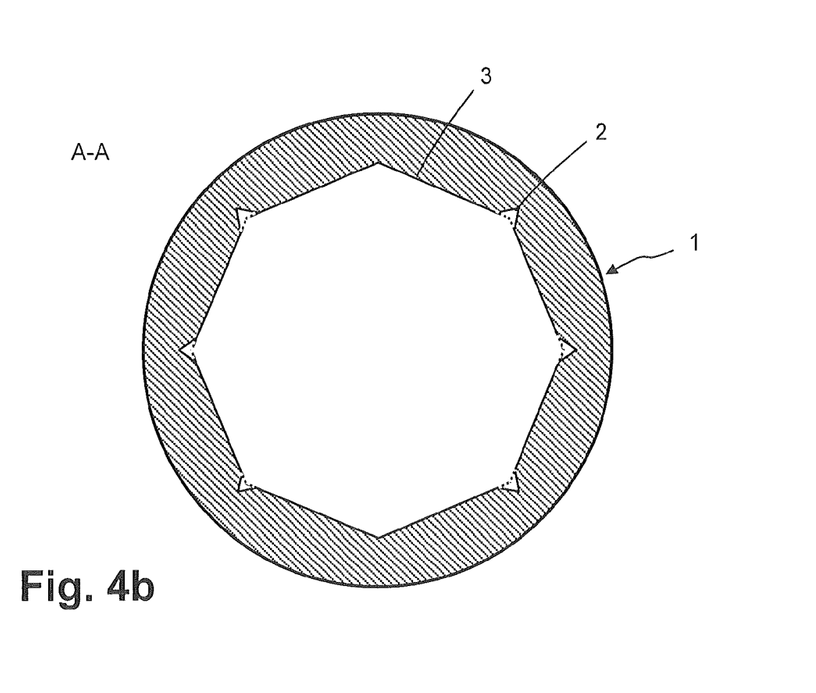
FIG. 4b is a cross-sectional top view drawing of a variation of the third embodiment of the threaded dental implant reduced to another socket arrangement with the first contact surfaces and with the second contact surfaces, wherein the second contact surfaces are in the form of six notches having the triangular cross-sectional shape.

FIGS. 4a to 4b are representations of a cross-sectional top view of variations according to a third preferred embodiment of the threaded dental implant, which is simplified in the drawing to a disk like cross-section of the socket arrangement, similar to that of FIGS. 2a to 3d. Substantially the same features apply herein as for the previous embodiments with a difference in the notches 2 as cross-sections of the ridges with the second contact surfaces 2a, 2b, having a triangular shape. Also the number and the position of notches or ridges can vary as explained in the previous embodiments.

Preferably, in the variations of the third embodiment, the two contact surfaces 2a and 2b are connected by a transition section (not shown) bridging the two surfaces in a way that the no acute angles are existing in the corners between contact surface 2a and 2b. The transition section is preferably curved.

This arrangement of the second contact surfaces 2a, 2b is less advantageous as compared with the rectangle notches 2 with respect to the forces applied by the ribs of the insertion tool 11. The force vector of torque is not perpendicular to the contact surfaces 2a and 2b, but oriented at a lower angle, which is more unfavorable with respect to jamming/welding of the insertion tool during implant insertion. As compared to the shape of notches 2 or ridges represented in FIGS. 2a to 3d, the shape of the notches 2 or ridges of the embodiments of FIGS. 4a to 4b ensures a minimal removal of material from the original contact surface 3. Therefore, a higher stability of the implant can be expected in parallel with a shorter milling or cold forming time of this structure.

Figure 5A:
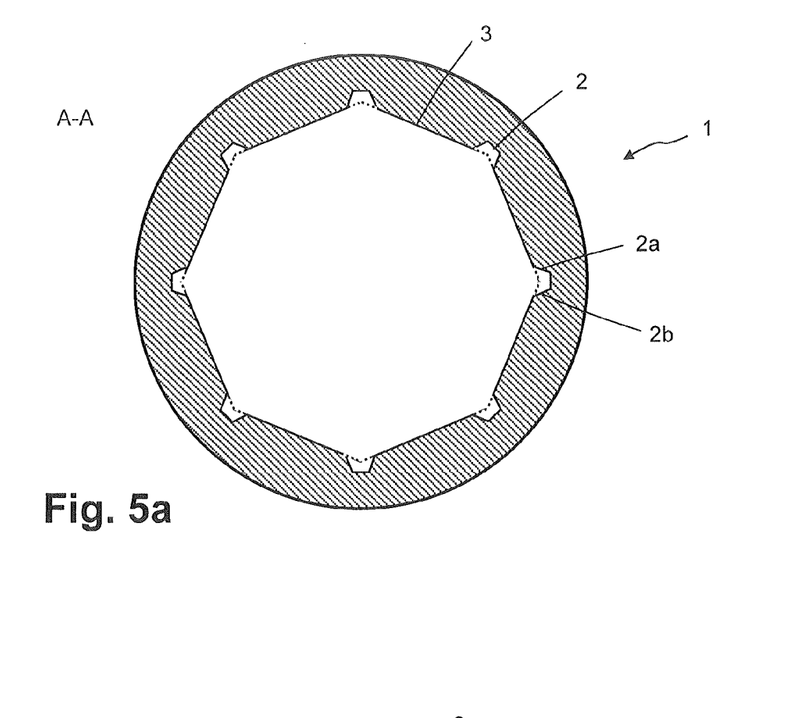
FIG. 5a is a cross-sectional top view drawing of a fourth embodiment of the threaded dental implant reduced to another socket arrangement with the first contact surfaces and with the second contact surfaces, wherein the second contact surfaces are in the form of six notches having a trapezoidal cross-sectional shape.
Figure 5B:
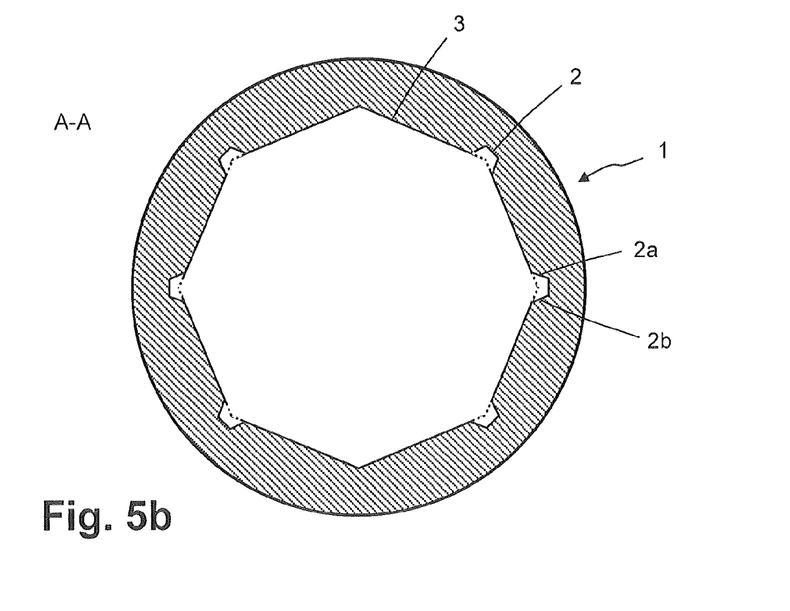
FIG. 5b is a variation of FIG. 5a with a lesser number of second contact surfaces.

FIGS. 5a to 5b are representations of a cross-sectional top view of variations according to a fourth preferred embodiment of the threaded dental implant, which is reduced in the drawing to a disk like cross-section of the socket arrangement, similar to that of FIGS. 2a to 4b. Substantially the same features apply herein as for the previous embodiments with a difference in the shape of the notches 2.

The latter embodiment of the invention differs from the previous ones in that the cross-section of the ridges is of trapezoidal shape with the second contact surfaces 2a, 2b forming the sides of the trapezoid. The trapezoidal shape is tapered in radial direction outwardly. This arrangement of the second contact surfaces 2a, 2b is less advantageous as compared with the rectangular notches 2 as regards the forces applied by the ribs of the insertion tool 11, more favorable than a triangular shape as the torque vector to the contact surfaces are 2a and 2b lies at a greater angle. In addition this trapezoidal shape is suitable for cold heading operations, and thus must not be milled as being more time consuming.

Another modified embodiment (not shown) with similar features to those of said fourth embodiment of FIGS. 5a to 5b, but wherein the trapezoidal shape is tapered in radial direction inwardly, is also imaginable. The latter variation has a better perpendicular shape in terms of the applied forces from the ribs of the insertion tool 11. The embodiment with inwardly tapered notches 2 with the second contact surfaces 2a, 2b perpendicular to the applied forces prevent a welding of the contact surfaces which would otherwise weld the contact surfaces if applied with a high tangential component.

In all described versions of the third and fourth embodiment shown in FIGS. 4a to 5b the angle between contact surface 2a and 2b can range between 30° and 90°, whereby the risk of welding the notches 2 and ridges during torque transmission increases with increasing angle.

FIGS. 2a to 5b show either four, six or eight notches 2 or ridges either located at sides of contact surface 3 or in the corners of contact surface. This number can be independent of the shape of the notches 2 or ridges and independent of the position of them with respect to the contact surface 3. In other words, according to the invention, combinations of any number or notches (equal or less to the number of sides of the polygon) with any positions of the notches (be it at the corners or the sides of the polygon) and with any shape of the notches described hereinabove is envisaged.

Preferably, in all embodiments of the invention the number of notches 2 is less than the number of the corners of the polygon of the first contact surfaces 3. The decreased number of notches increases the stability and solidness of the first section of the socket arrangement the implant, where no notch 2 is devised. Thus the implant can be featured with a higher solidness in certain lateral angular sections within the height 1a of the socket. In parallel milling time is reduced.

Figure 6:
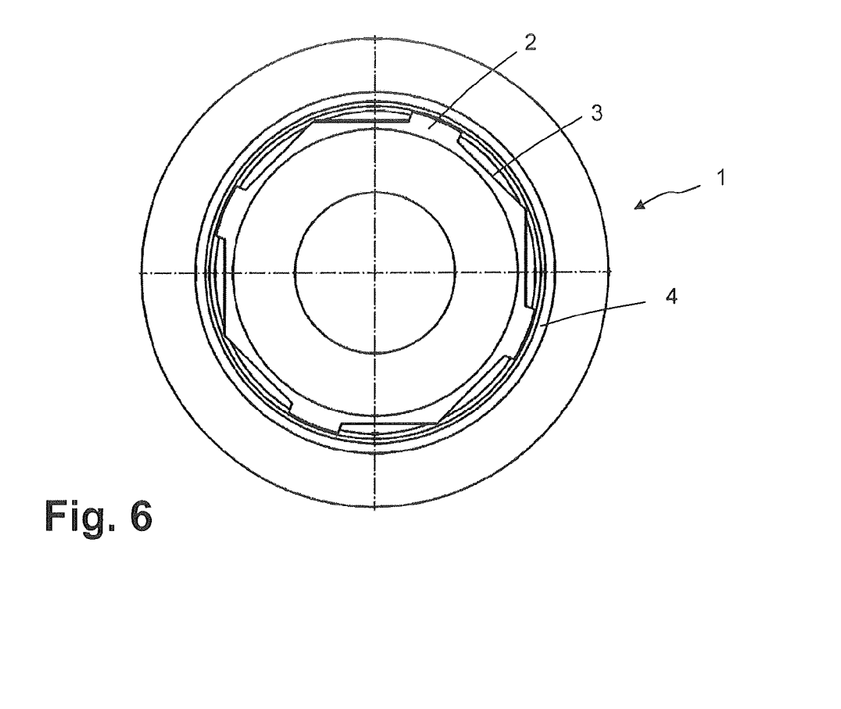
FIG. 6 is a top view drawing of the embodiment of FIG. 2c.

FIG. 6 is a drawing of a top view of the embodiment of FIG. 2c. As shown the four notches 2 are devised in a 90 degree angular placement within the polygonal shape of the first contact surfaces 3 being the octagon. The latter preferred embodiment combines both: a) a large radial diameter (diagonal) of the opposite notches 2 resulting in a long arm of a lever, and b) more solid areas of the first section of the socket arrangement resulting in a large area of the first contact surfaces and in a high stability and solidity of the implant 1.

Figure 7:
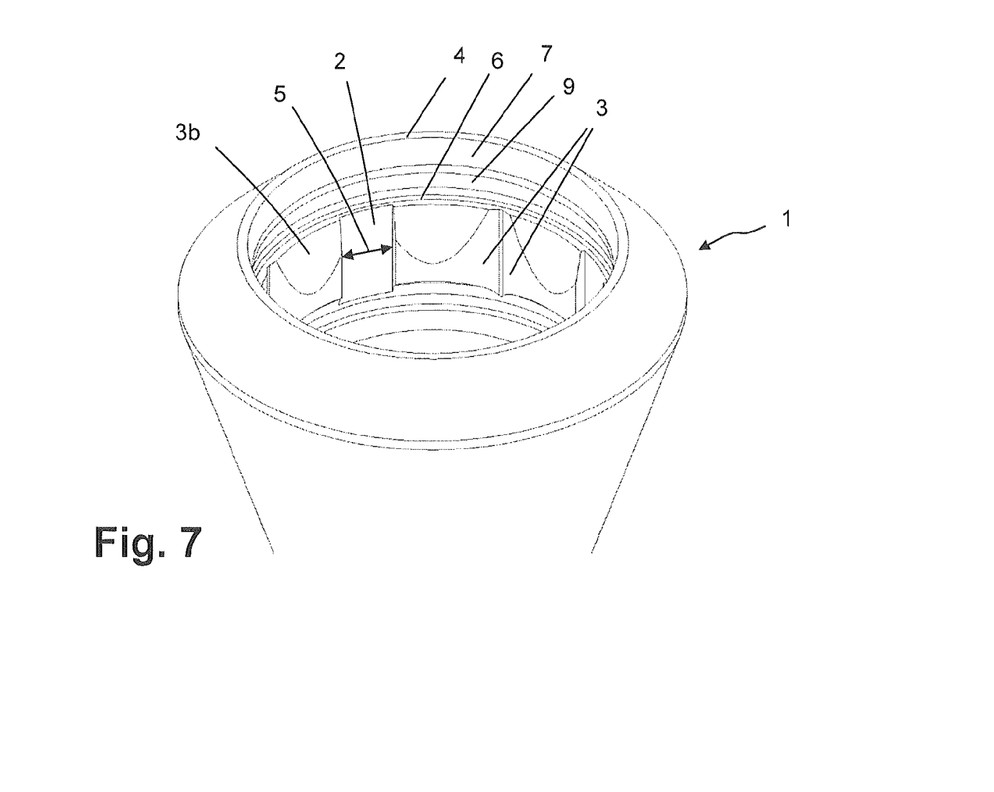
FIG. 7 is a perspective view of the fifth embodiment of the threaded dental implant.

FIG. 7 shows a perspective view of the embodiment of FIG. 6 or 2c with the preferably threaded dental implant 1, depicting the two respective second contact surfaces 2a and 2b having a notch width 5 as distance in between the two respective second contact surfaces 2a and 2b, the first contact surfaces 3 having a shape of the regular octagon, and a lower contact platform 6. As discussed above, the first contact surfaces 3 are devised as parallel contact surfaces. If the first contact surfaces 3 include slightly inclined sections, like the truncated conical sections 3b, such sections are slightly inclined towards the apical end of the implant, having a shape of a truncated pyramid, so as to allow a certain self-finding for the abutment during the insertion of the abutment in the implant 1. The truncated conical sections 3b are slightly cut out or eroded from a coronal part of the first contact surfaces 3, wherein the truncated conical sections 3b have a diameter of opposing sides which is slightly bigger than the inner distance between opposing sides of the first surfaces 3, with respect to a certain height along the longitudinal axis of the implant. The diameter of the truncated conical sections 3b between the opposing sides is smaller than the distances between the edges of the regular polygon, such that the edges remain and are not cut out. Preferably the lower contact platform 6 serves as contact surface for the insertion tool 11, such that a defined engagement occurs in the longitudinal direction of the implant 1 and the insertion tool 11. The lower contact platform 6 facilitates the introduction of the insertion tool 11 into notches 2 or ridges. The notch width 5 is preferably in the range of 0.4-0.7 mm and most preferably about 0.55 mm. A wider notch width 5 leads to a larger area of the second contact surfaces 2a, 2b, which is advantageous, but at the same time it leads also to smaller first contact surfaces 3 for the abutment, which is disadvantageous. Thus, the preferred notch width 5 in the range of 0.4-0.7 mm and most preferably of about 0.55 mm is a good compromise for the above conflicting requirements. A smaller notch width 5 leads also to less stable ribs of the insertion tool 11. As further shown in FIG. 7 the dental implant 1 comprises at its coronal end and following the coronal opening an upper conical section 7 having a defined taper.

Figure 7A:
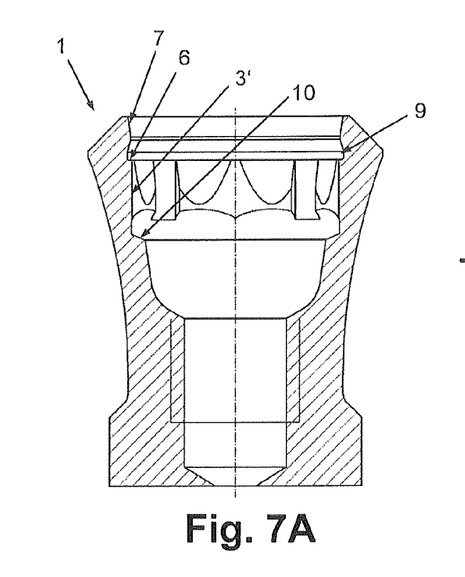
FIGS. 7a, 7c and 7e are drawings of side views of the embodiment of FIG. 7, depicting the socket arrangement parallel to the longitudinal axis (L-L').
Figure 7B:
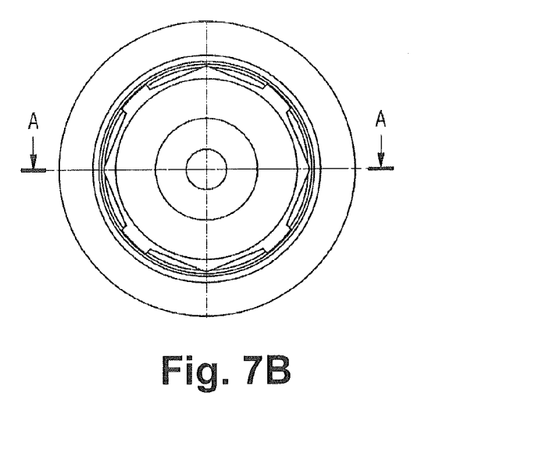
FIGS. 7b, 7d and 7f are drawings of top views of the embodiment of FIG. 7, depicting in addition the orientation of the longitudinal sections presented in FIGS. 7a, 7c and 7e.
Figure 7C:
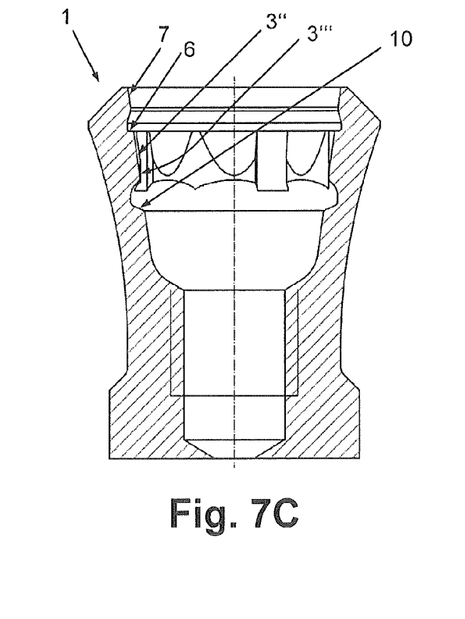
Figure 7D:
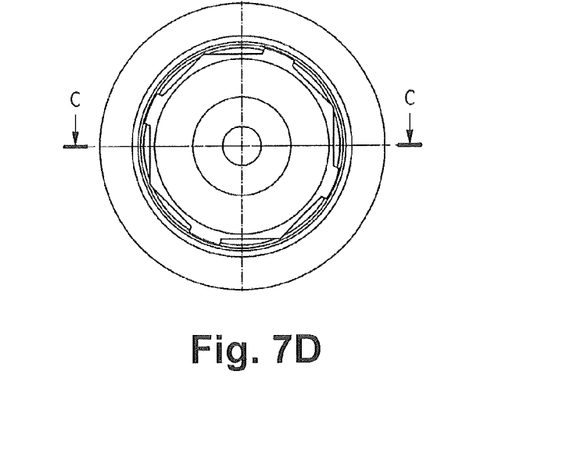
Figure 7E:
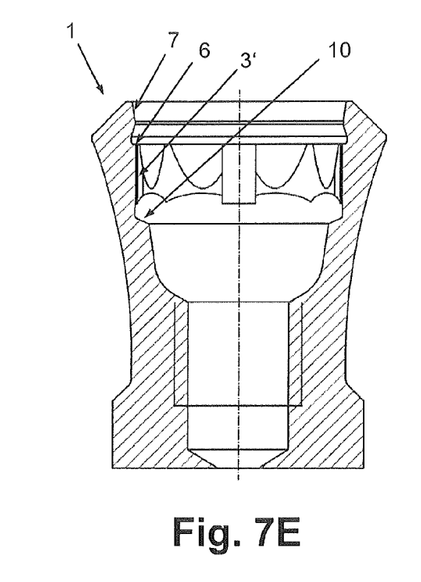
Figure 7F:
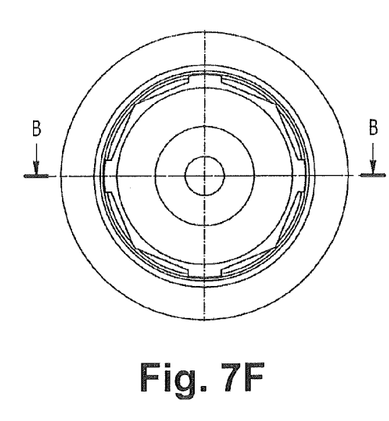

FIGS. 7a, 7c and 7e show detailed side views of the inner implant configuration (socket) of FIG. 6 while FIGS. 7b, 7d and 7f show the corresponding cuts in top view along the longitudinal axis of the inner implant configuration (socket) of FIG. 6. As shown in FIGS. 7a, 7c and 7e, starting from top of the implant shoulder, the upper conical section 7 has a taper (10°+/−5°; preferably 8° with respect to the longitudinal of the implant 1, followed by a short cylindrical section 8, followed by a first recess (undercut) 9, followed by the lower contact platform 6 which is substantially horizontal. In FIGS. 7a and 7e the lower contact platform 6 is followed by parallel walled sections 3' which form the first contact surfaces 3, whereas in FIG. 7c the lower contact platform 6 is followed by tapered walled section 3" having the same taper as the upper conical section 7 and forming the truncated conical sections 3b which extend apically before passing into parallel walled sections 3'". Further apically in all sections FIGS. 7a, 7c and 7e a second recess (undercut) 10 leads into the lower part of the inner implant socket.

This upper conical section 7 is not in contact to the insertion tool 11, but represents the sealing section towards the abutment. The first recess 9 has two functionalities: providing a platform for the mounting of the insertion tool 11 under conditions, where handling with bare hands is not possible. The lower contact platform 6 helps rotating the insertion tool 11 along its longitudinal section (almost frictionless) before finding the notches 2 that allow to engage with the ridges of the insertion device. Secondly the first recess 9 is used to engage with the C- or O-Ring of the insertion tool 11 to provide retention force towards the implant 1 in order to make sure that the two parts are firmly connected during transport (logistical) and during transport to the patience mouth (after unpacking). The retention force is however sufficiently low to allow easy disengagement with the implant after insertion of the implant.

While the features of the inner implant configuration (socket) of FIGS. 7a to 7f have been described in connection with the embodiment of FIG. 7 it should be appreciated that such features all equally applicable to the other embodiments herein described.

Figure 8:
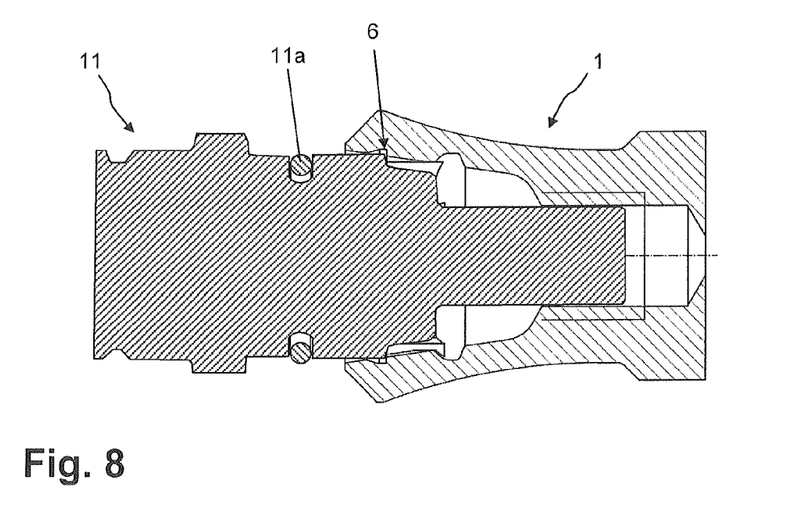
FIG. 8 is a cross-sectional side view of another embodiment of the threaded dental implant with an inserted insertion tool, wherein a lower contact platform is embodied within the implant and the corresponding contact surface is embodied in the insertion tool.

FIG. 8 is a cross-sectional side view of an embodiment of the implant 1 and the insertion tool 11 inserted therein, wherein it is depicted that the insertion tool 11 abuts against the lower contact platform 6 of the implant 1 and allows the insertion tool 11 to be rotated around its longitudinal axis allowing to find the axial position for engaging with the notches 2.

In all above embodiments, preferably, the polygonal shape is an octagon. In addition, in all above embodiments, preferably, the notches 2 or ridges, respectively, can be slightly curved in their corners for allowing an easier machining or production of the implant 1.

Preferably, in all above embodiments, the second contact surfaces of the notches 2 or within the ridges, respectively, are devised perpendicular to the applied forces by the ribs of the insertion tool 11 with a tolerance of preferably 10 degrees or even more preferred with a tolerance of 5 degrees.

Preferably, in all above embodiments, the first and the second section of the socket arrangement end substantially within the height 1a of the socket arrangement. But it is also imaginable that the height of the first and/or the second socket section is extended beyond the section defined by the height 1a. In this case there should be an overlap of at least 50% between the first and second socket sections for the sake of stability of the implant. Preferably, in all above embodiments, the socket arrangement is devised centric and along the longitudinal axis of the implant 1, such that both the first contact surfaces 3 and the second contact surfaces 2a, 2b are arranged to be axis symmetrical to the longitudinal axis.

Preferably an inner and an outer diameter of the lower contact platform 6, which is arranged horizontally perpendicular to the longitudinal center axis and coronally adjacent to the second section of the socket arrangement, are adapted to allow the ribs of the insertion tool 11 to rotatably glide on the lower contact platform 6 until the ribs are flush with the notches 2 and ridges, respectively.

The Insertion tool 11 is adapted, particularly concerning the apical force transmitting part thereof, to correspond and engage with the dental implant 1 in a secure and easy disengageable manner. The insertion tool 11 comprises ribs being adapted to correspond and engage with the second contact surfaces 2a, 2b, such that contact surfaces of the ribs correspond to said second contact surfaces 2a or 2b. If the insertion tool 11 is rotated in anti-clockwise direction the second contact surfaces 2a engage with the respective contact surfaces of the insertion tool 11; if the insertion tool 11 is rotated in clockwise direction the second contact surfaces 2b engage with other respective contact surfaces of the insertion tool 11. The notches 2 and ridges of the implant 1 are second anti-rotational means for engagement with the insertion tool 11 for transmitting the torque forces of the insertion of the implant 1 in the jawbone. The ribs are adapted that they do not become jammed or squeezed in between the opposite second contact surfaces 2a and 2a or between the opposite radial lateral surfaces 2c of the ridges of the implant 1. The ribs are adapted in material and strength to the torque forces which have to be transmitted. The apical end of the insertion tool 11 with the ribs is adapted to keep a distance to the first contact surfaces 3 of the implant 1, such that if a torque is applied and transmitted the first contact surfaces 3 are not pressed or could be deformed.

Preferably the insertion tool 11 comprises an O-ring adapted in diameter and strength to engage with an inner annular recess (the first recess 9) of the implant, such that a retention force on said implant 1 in its longitudinal direction is exerted during insertion in the patient's mouth. The O-ring or split C-Ring is further adapted that said retention force with the implant 1 is kept as little, such that the retention force is not affecting the position of the inserted implant 1 in the jawbone during a disengaging of the insertion tool 11. The O-Ring or C-Ring stands preferably for an interrupted or non-interrupted ring made of plastics, or metal, such as for instance of titanium.

Preferably the apical and force transmitting part of the insertion tool 11 is extended in apical direction by a lower annular section, wherein the lower annular section is adapted to engage rotatably with a bore of the threaded section 1b of the dental implant 1, such that an additional stability against tilting is provided.

Preferably the apical and force transmitting part of the insertion tool 11 is made of a hard material, such as to prevent a mechanical twisting thereof.

According to a preferred embodiment there is provided a dental implant intended to be screwed into the jawbone for supporting at least one abutment, and having a socket arrangement with a first and a second section with respective geometrical profiles, wherein the socket arrangement is devised to cooperate on the one hand with the abutment for rotationally securing the abutment in a determined position, and on the other hand with an insertion tool for screwing the implant in, wherein the socket arrangement is devised as a central internal socket with an opening at the coronal end of the dental implant and in direction of a longitudinal center axis of the implant, wherein the first section of the socket arrangement defines first contact surfaces and wherein the second section of the socket arrangement defines second contact surfaces, the first and the second contact surfaces being located substantially at the same height in respect to the longitudinal center axis of the implant, wherein the first contact surfaces form together, along an orthogonal cross-section taken at the longitudinal center axis of the implant at the coronal end of the first contact surfaces, a regular polygon which is partly interrupted by outwardly extending notches, the first contact surfaces being parallel or parallel and partly inclined with respect to the longitudinal center axis of the implant, the inclination being such as to taper inwardly from their coronal end, wherein interrupting and outwardly extending ridges emerge from the first contact surfaces, the ridges extending from the notches in an apical direction of the dental implant, the first contact surfaces being adapted to engage and rotationally secure the abutment, wherein the second contact surfaces extend from the notches within the ridges in the direction of the longitudinal center axis, the second contact surfaces being adapted to engage with the insertion tool, and wherein the notches are positioned at sides or at corners of the regular polygon, and wherein the regular polygon is preferably an octagon.

In the latter preferred embodiment, the notches are preferably shaped as squares or rectangles. In a further preferred aspect of the latter embodiment the notches are shaped as laterally slightly curved notches and wherein the respective ridges formed at the notches comprise at least one laterally curved surface being comprised between said second contact surfaces, and wherein preferably the laterally curved surface is shaped as circular arcs between said second contact surfaces.

Further, in the latter preferred embodiment, the notches may be shaped as triangles or as trapezoids.

Moreover, preferably, in the latter preferred embodiment, the polygon which may be an octagon can be intersected by a number of four, six or eight notches. Further, the polygon which may be an octagon can be intersected by a number of six notches and the notches may be arranged at the corners of the octagon. Preferably, in the latter preferred embodiment, the notches can be arranged at the corners of the polygon (or octagon if the polygon is embodied as an octagon). Alternatively, in the latter preferred embodiment, the notches may be arranged at the respective sides of the polygon (or octagon if the polygon is embodied as an octagon).

Preferably, in the latter preferred embodiment, said second contact surfaces are positioned within an area engaging with the insertion tool and the second contact surfaces are angled such that torque forces applied by respective contact surfaces of the insertion tool during a process of screwing the implant into the jawbone are perpendicular to the second contact surfaces; or preferably said second contact surfaces are angled perpendicularly to the torque forces of the insertion tool or perpendicular with a tolerance of equal or less than 45 degrees.

Preferably, in the latter preferred embodiment, said regular polygon (or octagon) has rounded corners and is substantially described by a number of sides corresponding to the first contact surfaces; and/or the ridges have rounded corners.

Preferably, in the latter preferred embodiment, the first contact surfaces starting at a coronal end of the implant and extending in apical direction have the same extension as the ridges and are devised in the same height as the ridges.

Preferably, in the latter preferred embodiment, an inner and an outer diameter of a lower contact platform, which is arranged horizontally perpendicular to the longitudinal center axis and coronally adjacent to the second section of the socket arrangement, are adapted to allow ribs of the insertion tool to rotatably glide on the lower contact platform until the ribs are flush with the ridges.

Preferably, in the latter preferred embodiment, the ridges are truncating into a tapered section.

The latter preferred dental implant can be used with a insertion tool, the insertion tool having an apical and force transmitting part which is engageable with the dental implant, the insertion tool having: ribs corresponding to and engageable with the second contact surfaces of the ridges of the implant, said ridges of the implant providing for second anti-rotational means for engagement with the insertion tool for transmitting insertion torque forces; and having a form fitting into a socket arrangement with first contact surfaces of the implant, said first contact surfaces providing for first anti-rotational means for keeping an abutment on the implant, said form of the insertion tool being configured so that it keeps a distance to the first surfaces or so that it comprises round parts at the first contact surfaces such that no torque is transmitted to said first contact surfaces.

Preferably, is the latter insertion tool, the lower end carries an O-ring or split C-ring, the O-ring or split C-ring having an outer diameter such that the O- or split C-ring engages with the socket arrangement of the implant, such that a retention force on said implant in its longitudinal direction is exerted during insertion in the patient's mouth, and such that the retention force is not affecting the position of the implant during a disengaging of the insertion tool.

Preferably, in the latter insertion tool, the apical and force transmitting part of the insertion tool is extended in apical direction by a lower annular section, wherein the lower annular section is adapted to engage rotatably with a bore of a threaded section of the dental implant, such that an additional stability against tilting is provided; and/or the apical and force transmitting part of the insertion tool is made of a hard material, such as to prevent a mechanical twisting thereof.

Where technical features mentioned in any claim are followed by reference signs, those reference signs have been included just for the sole purpose of increasing intelligibility of the claims and accordingly, such reference signs do not have any limiting effect on the scope of each element identified by way of example by such reference signs.

2 notch
2a, 2b second contact surface
2c lateral surface
3 first contact surfaces
3b truncated conical sections
3', 3", 3'" parallel walled sections
4 upper contact surface
5 notch width
6 lower contact platform
7 upper conical section
8 short cylindrical section
9 first recess (undercut)
10 second recess (undercut)
11 insertion tool
11a resilient O-Ring or a split C-Ring

The invention claimed is:
1. Dental implant intended to be screwed into the jawbone for supporting at least one abutment, and having a socket arrangement with a first and a second section with respective geometrical profiles,
wherein the socket arrangement is devised to cooperate on the one hand with the abutment for rotationally securing the abutment in a determined position, and on the other hand with an insertion tool for screwing the implant in;
wherein the socket arrangement is devised as a central internal socket with an opening at a coronal end of the dental implant and in direction of a longitudinal center axis of the implant;
wherein the first section of the socket arrangement defines first contact surfaces and wherein the second section of the socket arrangement defines second contact surfaces, the first and the second contact surfaces being located substantially at the same height in respect to the longitudinal center axis of the implant;
wherein the first contact surfaces form together, along an orthogonal cross-section taken at the longitudinal center axis of the implant at a coronal end of the first contact surfaces, a regular polygon which is partly interrupted by outwardly extending notches, the first contact surfaces being parallel or parallel and partly inclined with respect to the longitudinal center axis of the implant, inclination thereof to taper inwardly from their coronal end,
wherein interrupting and outwardly extending ridges emerge from the first contact surfaces, the ridges extending from the notches in an apical direction of the dental implant, the first contact surfaces being adapted to engage and rotationally secure the abutment;
wherein the second contact surfaces extend from the notches within the ridges in a direction of the longitudinal center axis, the second contact surfaces being adapted to engage with an insertion tool;
wherein the notches are positioned at sides or at corners of the regular polygon; and
wherein the regular polygon is an octagon.

2. Dental implant according to claim 1, wherein the notches are shaped as rectangles.

3. Dental implant according to claim 1, wherein the notches are shaped as laterally slightly curved notches and wherein the respective ridges formed at the notches comprise at least one laterally curved surface being comprised between the second contact surfaces, and wherein the laterally curved surface is shaped as circular arcs between the second contact surfaces; or wherein the notches are shaped as triangles or squares or trapezoids.

4. Dental implant according to claim 1, wherein the octagon is intersected by a number of four, six or eight notches.

5. Dental implant according to claim 1, wherein the octagon is intersected by a number of four or six notches and wherein the notches are arranged at the corners of the octagon.

6. Dental implant according to claim 1, wherein the second contact surfaces are positioned within an area engaging with the insertion tool and wherein second contact surfaces are angled such that torque forces applied by respective contact surfaces of the insertion tool during a process of screwing the implant into the jawbone are perpendicular to the second contact surfaces; or wherein the second contact surfaces are angled perpendicularly to torque forces of the insertion tool or perpendicular with a tolerance of equal or less than 45 degrees.

7. Dental implant according to claim 1, wherein the octagon has rounded corners and is substantially described by a number of sides corresponding to the first contact surfaces; and/or wherein the ridges have rounded corners.

8. Dental implant according to claim 1, wherein the first contact surfaces starting at a coronal end of the implant and extending in apical direction have the same extension as the ridges and are devised in the same height as the ridges.

9. Dental implant according to claim 1, wherein an inner and an outer diameter of a lower contact platform, which is arranged horizontally perpendicular to the longitudinal center axis and coronally adjacent to the second section of the socket arrangement, are adapted to allow ribs of the insertion tool to rotatably glide on the lower contact platform until the ribs are flush with the ridges.

10. Dental implant according to claim 1, wherein the ridges are truncating into a tapered section.

11. Dental implant according to claim 1, wherein the number of notches is less than the number of the corners of the octagon.

12. Insertion tool in combination with the dental implant of claim 1, the insertion tool having an apical and force transmitting part which is engageable with the dental implant, the insertion tool having:
   ribs corresponding to and engageable with the second contact surfaces of the ridges of the implant, the ridges of the implant providing for second antirotational means for engagement with the insertion tool for transmitting insertion torque forces; and
   a form fitting into a socket arrangement with first contact surfaces of the implant, the first contact surfaces providing for first anti-rotational means for keeping an abutment on the implant, a form of the insertion tool being configured so that it keeps a distance to the first surfaces or so that it comprises round parts at the first contact surfaces such that no torque is transmitted to the first contact surfaces.

13. Insertion tool according to claim 12, wherein a lower end carries an O-ring or split C-ring, the O-ring or split C-ring having an outer diameter such that the O- or split C-ring engages with the socket arrangement of the implant, such that a retention force on the implant in its longitudinal direction is exerted during insertion in the patient's mouth, and such that the retention force is not affecting the position of the implant during a disengaging of the insertion tool.

14. Insertion tool according to claim 12, wherein an apical and force transmitting part of the insertion tool is extended in apical direction by a lower annular section, wherein the lower annular section is adapted to engage rotatably with a bore of a threaded section of the dental implant, such that an additional stability against tilting is provided; and/or
   wherein the apical and force transmitting part of the insertion tool is made of a hard material to prevent a mechanical twisting thereof.

15. Insertion tool according to claim 12, wherein the number of ribs matches the number of the second contact surfaces.

* * * * *